US00PP27612P3

(12) United States Plant Patent
Dibley

(10) Patent No.: US PP27,612 P3
(45) Date of Patent: Jan. 24, 2017

(54) ***SPREPTOCARPUS* PLANT NAMED 'SLSGI21-0'**

(50) Latin Name: ***Streptocarpus* hybrid**
Varietal Denomination: SLSGI21-0

(71) Applicant: Lynne Dibley, Ruthin (GB)

(72) Inventor: Lynne Dibley, Ruthin (GB)

(73) Assignee: Dibley's Nurseries (GB)

( * ) Notice: Subject to any disclaimer, the term of this patent is extended or adjusted under 35 U.S.C. 154(b) by 58 days.

(21) Appl. No.: 14/545,506

(22) Filed: May 12, 2015

(65) Prior Publication Data

US 2016/0338246 P1 Nov. 17, 2016

(51) Int. Cl.
*A01H 5/02* (2006.01)

(52) U.S. Cl.
USPC ..... Plt./333

(58) Field of Classification Search
USPC ..... Plt./333
See application file for complete search history.

*Primary Examiner* — Anne Grunberg
(74) *Attorney, Agent, or Firm* — Cassandra Bright

(57) ABSTRACT

A new and distinct *Streptocarpus* cultivar named 'SLSGI21-0' is disclosed, characterized by flowers colored purple and purple-violet with white streaks and flecks. Plants are compact and highly floriferous with many flowers per inflorescence. Inflorescences are uniquely short. The new variety is a *Streptocarpus*, suitable as an outdoor garden or container plant.

2 Drawing Sheets

Figure 1:
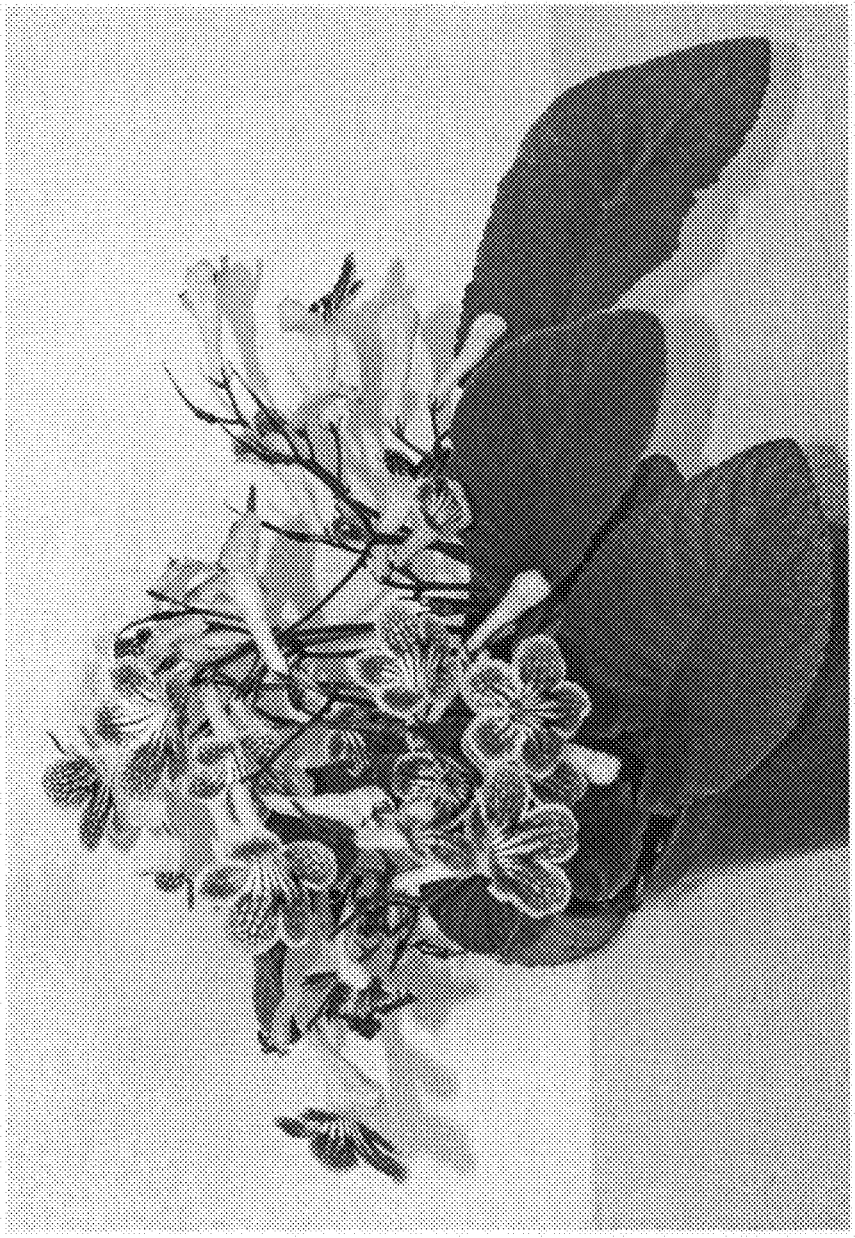

Latin name of the genus and species: *Streptocarpus* hybrid.

Variety denomination: 'SLSGI21-0'.

The new *Streptocarpus* cultivar is the product of a planned breeding program by the inventor Lynne Dibley, a citizen of Great Britain. The breeding program was carried out at a commercial nursery in Ruthin, United Kingdom. The objective of the breeding program was to develop new *Streptocarpus* varieties for ornamental purposes.

The new variety resulted from the crossing of the seed parent, an unnamed, unpatented proprietary *Streptocarpus* seedling with the pollen parent, an unnamed, unpatented proprietary *Streptocarpus* seedling in Spring of 2012. The new variety was discovered in January 2013 by the inventor in a group of seedlings resulting from the 2012 crossing, at a commercial nursery in Ruthin, United Kingdom.

Asexual reproduction of the new cultivar 'SLSGI21-0' by vegetative cuttings was first performed at a commercial greenhouse in Ruthin, United Kingdom in May 2013. Subsequently at least three generations have been produced from vegetative cuttings, and have shown that the unique features of this cultivar are stable and reproduced true to type.

SUMMARY OF THE INVENTION

The cultivar 'SLSGI21-0' has not observed under all possible environmental conditions. The phenotype may vary somewhat with variations in environment such as temperature, day length and light intensity, without however, any variance in genotype.

The following traits have been repeatedly observed and are determined to be the unique characteristics of 'SLSGI21-0'. These characteristics in combination distinguish 'SLSGI21-0' as a new and distinct *Streptocarpus* cultivar:

1. Unique flower coloration of Violet and Purple-Violet with White flecks and striping.
2. Compact plant habit.

3. Many flowers per inflorescence, up to 8 observed.
4. High flower count per plant.
5. Short inflorescences.

COMPARISON TO THE PARENT VARIETIES

Plants of the new cultivar 'SLSGI21-0' are similar in most horticultural characteristics to plants of the unnamed, unpatented proprietary seed parent. However, the new variety differs in the following:

1. The new variety has a larger overall flower size.
2. The new variety has shorter inflorescences.
3. The new variety is more floriferous.
4. The new variety has a different pattern of flower markings.

Plants of the new cultivar 'SLSGI21-0' are similar in most horticultural characteristics to plants of the unnamed, unpatented proprietary pollen parent. However, the new variety differs in the following:

1. The new variety has a larger overall flower size.
2. The new variety has shorter inflorescences.
3. The new variety has larger leaves than the pollen parent
4. The new variety has a different pattern of flower markings.

COMPARISON TO COMMERCIAL VARIETY

The new cultivar can be compared to the commercial variety 'Celebration', unpatented. Plants of the two cultivars are similar in most horticultural characteristics, however, plants of 'SLSGI21-0' differ in the following:

1. The new variety has a larger overall flower size.
2. The new variety has shorter inflorescences.
3. The new variety produces flowers colored White with Violet and Purple-Violet, this comparator produces pink with white flowers.
4. The new variety begins flowering earlier than this comparator.

The new cultivar can be compared to the commercial variety 'Bethan', unpatented. Plants of the two cultivars are similar in most horticultural characteristics, however, plants of 'SLSGI21-0' differ in the following:

1. The new variety has a larger overall flower size.
2. The new variety has shorter inflorescences.
3. The new variety produces flowers of a darker color than 'Bethan'.
4. The new variety has a different pattern of streaks and flecks to the flowers.

BRIEF DESCRIPTION OF THE PHOTOGRAPHS

The accompanying photograph in FIG. 1 illustrates in full color a typical plant of 'SLSGI21-0' grown in a greenhouse, in a 6 inch commercial pot.

Figure 2:
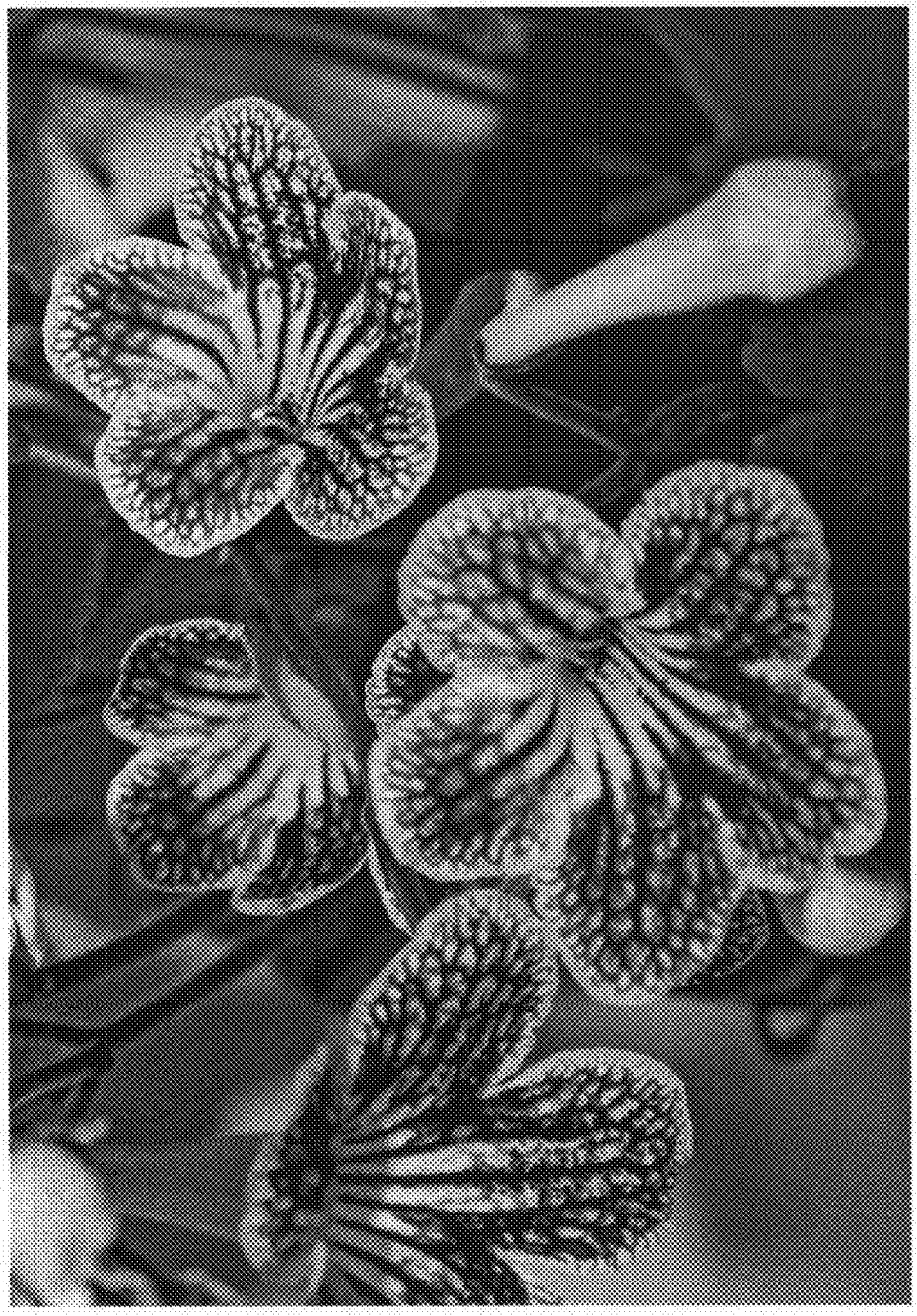

FIG. 2 illustrates typical flowers of 'SLSGI21-0'. Age of the plant photographed is approximately 20 weeks from a rooted plantlet. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 except where general terms of ordinary dictionary significance are used. The following observations and measurement describe 'SLSGI21-0' plants grown in a commercial greenhouse in Santa Paula, Calif. The growing temperature ranged from approximately 12° C. to 32° C. The greenhouse is subject to partial shade. General light conditions are bright, normal sunlight with some shade during the brightest part of the day. Measurements and numerical values represent averages of typical plant types.

Botanical classification: *Streptocarpus* hybrid 'SLSGI21-0'.

PROPAGATION

Time to initiate roots: About 20 to 25 days at approximately 21 to 25° C.

Root description: Fine, fibrous.

PLANT

Growth habit: Upright with large basally occurring, outwardly arching foliage.

Age of the plant described: Approximately 20 weeks from a well rooted cutting.

Pot size of plant described: 6 inch pot

Height: Approximately 14 cm from soil line to top of foliar plane. Approximately 21 cm to top of highest flower.

Plant spread: Approximately 33 cm at widest point.

Growth rate: Moderate.

Branching characteristics: Basal rosettes of foliate, no stem, no branches.

FOLIAGE

Leaf:

*Arrangement*.—Rosette.

*Quantity*.—Average 10 to 18 leaves.

*Average length*.—Approximately 18.0 cm.

*Average width*.—Approximately 8.9 cm.

*Shape of blade*.—Elliptic.

*Apex*.—Acute.

*Base*.—Attenuate.

*Margin*.—Crenate.

*Appearance of top surface*.—Matte.

*Appearance of top surface*.—Matte.

*Pubescence*.—Very short, less than 1 mm hairs, densely covering top and bottom leaf surfaces.

*Aspect*.—Undulating, overall leaf, including petiole, reflexes downward in older foliage.

*Color*.—Young foliage upper side: Near RHS Green 137B. Young foliage under side: Near RHS Green 138B. Mature foliage upper side: Near RHS Green 137A. Mature foliage under side: Near RHS Green 138B.

*Venation*.—Type: Pinnate. Venation color upper side: Near RHS Yellow-Green 144D. Venation color under side: Near RHS Yellow-Green 14C, heavily flushed Greyed-Purple N186C.

*Petiole*.—Not present, leaves sessile.

FLOWER

Natural flowering season: Continuous.

Inflorescence and flower type and habit: Racemes of asymmetrical funnel shaped flowers.

Inflorescence longevity on plant: At least 2 weeks before any significant change is observed.

Approximate quantity of flowers per plant: Approximately 30 to 75 mature and immature flowers per plant.

Flowers persistent:

Inflorescence:

*Diameter of entire inflorescence*.—Approximately 7.0 cm.

*Depth of inflorescence*.—Approximately 8.0 cm.

*Flowers per inflorescence*.—Typical average to 3 to 8.

*Inflorescence per plant*.—Average 15.

Individual flower bud:

*Shape*.—Tubular, with spherical apex.

*Length*.—Approximately 3.0 cm.

*Diameter*.—Approximately 1.1 cm.

*Color*.—Near RHS White N155A, distal end flushed Violet 83D.

Flowers:

*Flower length*.—5.5 cm.

*Flower width*.—3.5 cm.

*Upper petals* (*upper lip*).—Number: 2, fused together at base. Length: 1.2 cm. Width: 1.5 cm. Shape: Obicular. Apex: Obtuse. Margin: Very shallow irregular crenate. Texture: Velvety, all surfaces. Pubescent outer surface. Color: When opening: Inner surface: Near RHS Violet 84A, but brighter. Flecked with Purple-Violet N81A. Streaked with White N155A. Outer surface: Near White N155A, flushed Purple N79D. Fully opened: Inner surface: Close to a color between RHS Purple-Violet N81A and Violet 83A. Streaked with White N155C. Outer surface: Near White N155C, faint muddled stripes near Violet 83A. Aging: Inner surface: Near RHS Purple N79A and Greyed-Purple N186B, with streaks and flecks of White N155C. Outer surface: Near White N155C, faint muddled stripes near Violet 83A.

*Lower petals* (*lower lip*).—Quantity: 3. Length: 2.0 cm. Width: 1.5 cm. Shape: Somewhat elongated orbicular, fused at base. Apex shape: Obtuse. Margin: Shallow crenate, undulating. Texture: Velvety, all surfaces. Pubescent outer surface. Color: When opening: Inner surface: RHS Yellow 10A. Outer surface: RHS Purple 77A. Fully opened: Inner surface: RHS Yellow 2C, very faint flushing near margin Purple 77B. Outer surface: RHS Purple 77A. Aging: Inner surface: RHS Green-Yellow 1A. Outer surface: RHS Purple N79C.

*Throat*.—Length: 3.5 cm. Width: 1 cm, at widest point. Texture: glabrous, shiny inner surface. Outer surface pubescent. Color: When opening: Inner surface: Striped, RHS White N155C and Purple N79A. Outer surface: RHS Purple N79B. Fully opened: Inner surface: Striped, RHS White N155C and Purple N79A. Outer surface: RHS Purple N79D. Aging: Inner surface: Striped, RHS White N155C and Purple N79A. Outer surface: RHS Purple N79D with faint streaks White N155C.

Sepals:

*Quantity*.—Average 5.
*Shape*.—Narrow deltate, base fused.
*Length*.—Approximately 0.6 cm.
*Width*.—Approximately 0.3 cm.
*Apex*.—Acute.
*Base*.—Fused.
*Margin*.—Entire.
*Texture*.—Highly pubescent, all surfaces.
*Color*.—Upper Surface: Near RHS Green 137A, flushed Greyed-Purple N186B. Lower Surface: Near RHS Green 137A, flushed Greyed-Purple N186B.

Peduncle:

*Length*.—Average range 5 to 8 cm, before first branching.
*Diameter*.—Approximately 0.4 cm.
*Texture*.—Densely pubescent.
*Color*.—Near RHS Yellow-Green 146B, base flushed near Greyed-Purple N186C.
*Orientation*.—Approximately 90 to 75 degree angle from rosette.

Pedicel:

*Length*.—Average range 0.7 cm to 1.8 cm.
*Diameter*.—Approximately 0.3 cm.
*Texture*.—Soft, dense pubescence.
*Color*.—Near RHS Yellow-Green 146C, base flushed near Greyed-Purple N186B.
*Orientation*.—Approximately 30 to 45 degree angle from peduncle. Straight, or slightly outwardly curved.

Fragrance: None.

REPRODUCTIVE ORGANS

Stamens:

*Number*.—2.
*Filament length*.—Approximately 0.7 cm, unfused section.

Anthers:

*Length*.—Approximately 0.2 cm.
*Shape*.—Bi-lobed.
*Color*.—Near RHS White 155C.
*Pollen*.—Scant, colored near White 155C.

Pistil:

*Number*.—1.
*Length*.—Approximately 3.0 cm.
*Style*.—Length: Approximately 1.8 cm. Color: Near RHS Greyed-Purple N187B.
*Stigma*.—Shape: Bifurcate. Color: Near RHS Greyed-Purple N187D.

OTHER CHARACTERISTICS

Seeds and fruits: Not observed.

Disease/pest resistance: Neither resistant nor susceptible to normal diseases and pests of *Streptocarpus*.

Temperature tolerance: USDA zones 9-11.

What is claimed is:

1. A new and distinct cultivar of *Streptocarpus* plant named 'SLSGI21-0' as herein illustrated and described.

* * * * *